(12) United States Patent
Hsieh et al.

(10) Patent No.: US 7,242,749 B2
(45) Date of Patent: Jul. 10, 2007

(54) METHODS AND SYSTEMS FOR DYNAMIC PITCH HELICAL SCANNING

(75) Inventors: Jiang Hsieh, Brookfield, WI (US); Alexander Katsevich, Oviedo, FL (US); Samit Kumar Basu, Niskayuna, NY (US)

(73) Assignee: General Electric Company, Schenectady, NY (US)

( * ) Notice: Subject to any disclaimer, the term of this patent is extended or adjusted under 35 U.S.C. 154(b) by 0 days.

(21) Appl. No.: 11/273,851

(22) Filed: Nov. 15, 2005

(65) Prior Publication Data

US 2007/0110211 A1 May 17, 2007

(51) Int. Cl.
*G21K 1/04* (2006.01)

(52) U.S. Cl. ............................ 378/150; 378/16; 378/15

(58) Field of Classification Search ................ 378/4, 378/15, 16, 20, 145, 147, 150, 151, 62
See application file for complete search history.

(56) References Cited

U.S. PATENT DOCUMENTS

| | | | |
|---|---|---|---|
| 3,643,095 A | 2/1972 | Shuster | 378/151 |
| 3,793,520 A | 2/1974 | Grenier | 250/366 |
| 3,863,073 A | 1/1975 | Wagner | 378/91 |
| 3,936,647 A | 2/1976 | Fekete | 378/153 |
| 4,101,768 A | 7/1978 | Lill | 378/7 |
| 4,143,273 A | 3/1979 | Richey et al. | 378/7 |
| 4,246,488 A | 1/1981 | Hura | 378/151 |
| 4,321,473 A | 3/1982 | Albert | 378/149 |
| 4,389,730 A | 6/1983 | Cutter | 378/153 |
| 4,859,852 A | 8/1989 | Genna et al. | 250/363.1 |
| 5,127,030 A | 6/1992 | Annis et al. | 378/150 |
| 5,442,675 A | 8/1995 | Swerdloff et al. | 378/65 |
| 5,745,279 A | 4/1998 | Ciscato et al. | 359/233 |
| 5,748,703 A | 5/1998 | Cosman | 378/152 |
| 5,818,902 A | 10/1998 | Yu | 378/65 |
| 6,173,039 B1 | 1/2001 | Hampel et al. | 378/150 |
| 6,298,117 B1 | 10/2001 | Hampel et al. | 378/150 |
| 6,353,227 B1 | 3/2002 | Boxen | 250/363.1 |
| 6,449,340 B1 | 9/2002 | Tybinkowski et al. | 378/150 |
| 6,483,894 B2 | 11/2002 | Hartick et al. | 378/147 |
| 6,502,985 B1 | 1/2003 | Garland et al. | 378/207 |
| 6,507,642 B2 | 1/2003 | Fujishige et al. | 378/151 |
| 6,647,092 B2 | 11/2003 | Eberhard et al. | 378/65 |
| 6,807,250 B2 | 10/2004 | Wang et al. | 378/63 |
| 6,836,280 B2 | 12/2004 | Cannon et al. | 347/242 |
| 6,980,623 B2 | 12/2005 | Dunham et al. | 378/19 |
| 7,113,570 B2 * | 9/2006 | Toth et al. | 378/150 |

* cited by examiner

*Primary Examiner*—Courtney Thomas
(74) *Attorney, Agent, or Firm*—Carl B. Horton, Esq.; Armstrong Teasdale LLP (57) ABSTRACT

Methods and systems for controlling x-ray exposure during a dynamic pitch helical scan using a translatable table are provided. The system includes a collimator positioned between an x-ray source and an object to be scanned configured to shutter an x-ray fan beam generated by the x-ray source to at least one of translate the x-ray fan beam along a z-axis of the scan and vary the width of the x-ray beam along the z-axis, and a collimator controller configured to dynamically position the collimator using at least one of predetermined trajectory of the translatable table and a current position of the translatable table.

20 Claims, 6 Drawing Sheets

METHODS AND SYSTEMS FOR DYNAMIC PITCH HELICAL SCANNING

BACKGROUND OF THE INVENTION

This invention relates generally to scanning imaging systems, and more particularly to the production of images by scanning imaging systems having an x-ray beam width with a dynamically changeable width.

In at least one known CT imaging system configuration, an x-ray source projects a fan-shaped beam which is collimated to lie within an X-Y plane of a Cartesian coordinate system and generally referred to as the "imaging plane". The x-ray beam passes through the object being imaged, such as a patient. The beam, after being attenuated by the object, impinges upon an array of radiation detectors. The intensity of the attenuated beam radiation received at the detector array is dependent upon the attenuation of the x-ray beam by the object. Each detector element of the array produces a separate electrical signal that is a measurement of the beam attenuation at the detector location. The attenuation measurements from all the detectors are acquired separately to produce a transmission profile.

In known third generation CT systems, the x-ray source and the detector array are rotated with a gantry within the imaging plane and around the object to be imaged so that the angle at which the x-ray beam intersects the object constantly changes. A group of x-ray attenuation measurements, i.e., projection data, from the detector array at one gantry angle is referred to as a "view". A "scan" of the object comprises a set of views made at different gantry angles, or view angles, during one revolution of the x-ray source and detector.

In an axial scan, the projection data is processed to construct an image that corresponds to a two dimensional slice taken through the object. One method for reconstructing an image from a set of projection data is referred to in the art as the filtered back projection technique. This process converts the attenuation measurements from a scan into integers called "CT numbers" or "Hounsfield units", which are used to control the brightness of a corresponding pixel on a display.

To reduce the total scan time required for multiple slices, a "helical" scan may be performed. To perform a "helical" scan, the patient is moved in the z-axis synchronously with the rotation of the gantry, while the data for the prescribed number of slices is acquired. Such a system generates a single helix from a fan beam helical scan. The helix mapped out by the fan beam yields projection data from which images in each prescribed slice may be reconstructed. In addition to reducing scan time, helical scanning provides other advantages such as better use of injected contrast, improved image reconstruction at arbitrary locations, and better three-dimensional images.

To further reduce the total acquisition time, multi-slice CT has been introduced. In multi-slice CT, multiple rows of projection data are acquired simultaneously at any time instant. When combined with helical scan mode, the system generates a single helix of cone beam projection data. Similar to the single slice helical weighting scheme, the projection data can be "weighted" prior to filtered back-projection. Thus, one technical effect is the generation of a volumetric CT three-dimensional (3D) image of a scanned object.

Multislice CT systems are used to obtain data for an increased number of slices during a scan. Known multislice systems typically include detectors generally known as 3-D detectors. With such 3-D detectors, a plurality of detector elements form separate channels arranged in columns and rows. Each row of detectors forms a separate slice. For example, a two slice detector has two rows of detector elements, and a four slice detector has four rows of detector elements. During a multislice scan, multiple rows of detector cells are simultaneously impinged by the x-ray beam, and therefore data for several slices is obtained.

In known CT systems, the x-ray beam from the x-ray source is projected through a pre-patient collimating device, or collimator, that defines the x-ray beam profile in the patient axis, or z-axis. The collimator includes x-ray absorbing material with an aperture therein for restricting the x-ray beam. The process of restricting the x-ray beam to the desired fan beam profile is termed "collimation".

With respect to restricting the x-ray beam, known collimators typically include two opposing metallic blades or eccentric cams that may be opened and closed to change the aperture width. The fan beam "thickness", as measured along the z-axis, can be selected by adjusting the blade or cam orientation. The blades or cams also may be moved in a same direction to displace the centerline of the aperture. Changing the aperture centerline changes the fan beam angle with respect to the z-axis.

An imaging system that is capable of acquiring and reconstructing data when the translational pitch is modulated during the scan enables new applications and imaging protocols. However, the width of the X-ray beam does not change dynamically to coincide with the dynamically changing pitch.

BRIEF DESCRIPTION OF THE INVENTION

In one embodiment, a collimation system for controlling x-ray exposure during a dynamic pitch helical scan using a translatable table is provided. The system includes a collimator positioned between an x-ray source and an object to be scanned configured to shutter an x-ray fan beam generated by the x-ray source to at least one of translate the x-ray fan beam along a z-axis of the scan and vary the width of the x-ray beam along the z-axis, and a collimator controller configured to dynamically position the collimator using at least one of predetermined trajectory of the translatable table and a current position of the translatable table.

In another embodiment, a system for reducing x-ray exposure in a computed tomography (CT) system including an x-ray source, a detector array comprising a plurality of detector cells extending in a z-axis, and a pre-patient collimator is provided. The system is configured to determine a position of a patient table along the z-axis, and position said collimator to define a thickness of a fan beam to be directed towards an object to be imaged using at least one of the position of the patient table and a predetermined table trajectory.

In yet another embodiment, a method of controlling x-ray dosage in a computed tomography (CT) system is provided. The CT system includes a patient table translatable along a z-axis at a dynamically changeable rate and a collimator that defines an aperture. The method includes receiving data concerning a scan trajectory of the patient table, determining an amount of collimation on the detector using a selected image reconstruction algorithm requirement, and positioning the collimator aperture such that the determined collimation is maintained during the scan.

DETAILED DESCRIPTION OF THE INVENTION

As used herein, an element or step recited in the singular and proceeded with the word "a" or "an" should be understood as not excluding plural said elements or steps, unless such exclusion is explicitly recited. Furthermore, references to "one embodiment" of the present invention are not intended to be interpreted as excluding the existence of additional embodiments that also incorporate the recited features.

Also as used herein, the phrase "reconstructing an image" is not intended to exclude embodiments of the present invention in which data representing an image is generated but a viewable image is not. Therefore, as used herein the term "image" broadly refers to both viewable images and data representing a viewable image. However, many embodiments generate (or are configured to generate) at least one viewable image.

Further as used herein, the term "dynamical helical scan" refers to a helical scan in which data is collected while the pitch of the scan varies. More particularly, in configurations of the present invention, a translatable table holding an object during a scan is accelerated or decelerated while a scan is taking place to produce a variable pitch scan. For purposes of the present invention, it does not matter whether the acceleration or deceleration is intentional, incidental, or entirely unintentional, although in the configurations described herein, it is intentional.

Figure 1:
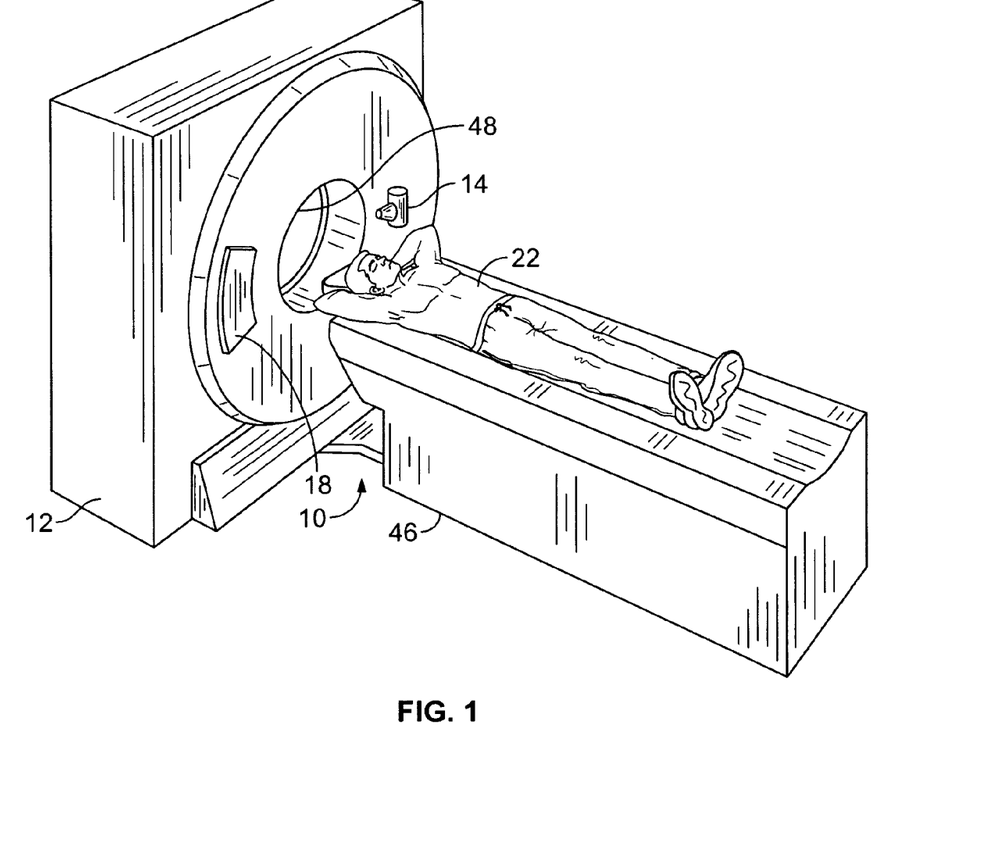
FIG. 1 is a pictorial view of a multi slice volumetric CT imaging system.
Figure 2:
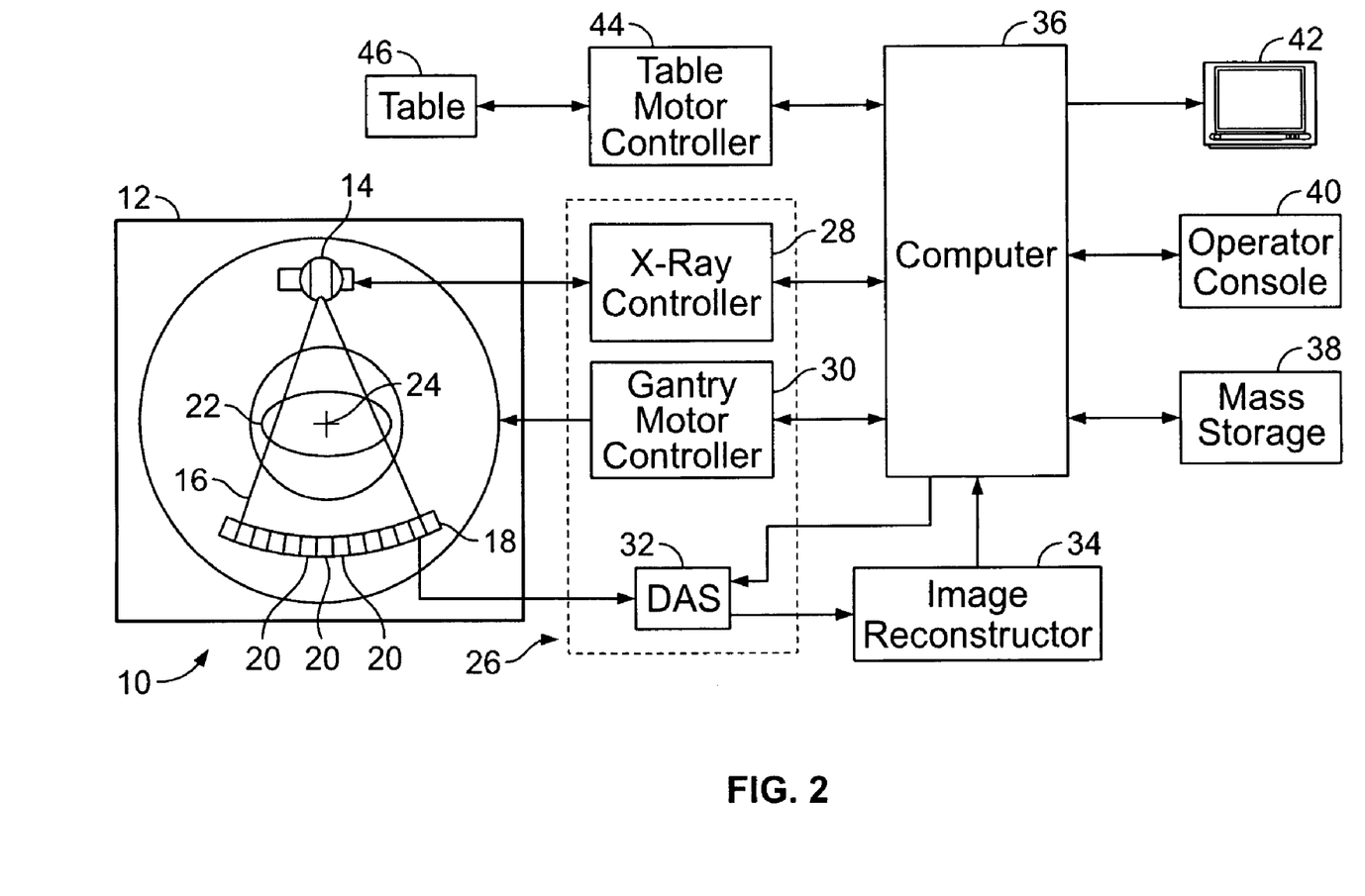
FIG. 2 is a block schematic diagram of the multi slice volumetric CT imaging system illustrated in FIG. 1.

FIG. 1 is a pictorial view of a multi slice volumetric CT imaging system 10. FIG. 2 is a block schematic diagram of CT imaging system 10 illustrated in FIG. 1. In the exemplary embodiment, a CT imaging system 10, is shown as including a gantry 12 representative of a "third generation" CT imaging system. Gantry 12 has a radiation source 14 that projects a cone beam 16 of X-rays toward a detector array 18 on the opposite side of gantry 12.

Detector array 18 is formed by a plurality of detector rows (not shown) including a plurality of detector modules 20 which together sense the projected X-ray beams that pass through an object, such as a medical patient 22. Each detector module 20 includes detector elements (not visible) that produce an electrical signal that represents the intensity of an impinging radiation beam and hence the attenuation of the beam as it passes through object or patient 22. A CT imaging system 10 having a multislice detector array 18 is capable of providing a plurality of images representative of patient 22. Each image of the plurality of images corresponds to a separate "slice" of the volume. The "thickness" or aperture of the slice is dependent upon the thickness of the detector rows.

During a scan to acquire radiation projection data, gantry 12 and the components mounted thereon rotate about a center of rotation 24. FIG. 2 shows only a single row of detector elements (i.e., a detector row). However, multislice detector array 18 includes a plurality of parallel detector rows of detector elements such that projection data corresponding to a plurality of quasi-parallel or parallel slices can be acquired simultaneously during a scan.

Rotation of gantry 12 and the operation of radiation source 14 are governed by a control mechanism 26 of CT imaging system 10. Control mechanism 26 includes a radiation controller 28 that provides power and timing signals to radiation source 14 and a gantry motor controller 30 that controls the rotational speed and position of gantry 12. A data acquisition system (DAS) 32 in control mechanism 26 samples analog data from detector elements and converts the data to digital signals for subsequent processing. An image reconstructor 34 receives sampled and digitized radiation data from DAS 32 and performs high-speed image reconstruction. The reconstructed image is applied as an input to a computer 36 which stores the image in a mass storage device 38.

Computer 36 also receives commands and scanning parameters from an operator via console 40 that has a keyboard. An associated display 42 allows the operator to observe the reconstructed image and other data from computer 36. The operator supplied commands and parameters are used by computer 36 to provide control signals and information to DAS 32, radiation controller 28, and gantry motor controller 30. In addition, computer 36 operates a table motor controller 44 which controls a motorized translatable table 46 to position patient 22 in gantry 12. Particularly, translatable table 46 moves portions of patient 22 through gantry opening 48.

In one embodiment, computer 36 includes a device 50, for example, a floppy disk drive or CD-ROM drive, for reading instructions and/or data from a computer-readable medium, such as a floppy disk or CD-ROM. In another embodiment, computer 36 executes instructions stored in firmware (not shown). Generally, a processor in at least one of DAS 32, reconstructor 34, and computer 36 shown in FIG. 2 is programmed to execute the processes described below. Of course, the method is not limited to practice in CT imaging system 10 and can be utilized in connection with many other types and variations of imaging systems. In one embodiment, computer 36 is programmed to perform functions described herein. Accordingly, as used herein, the term computer is not limited to just those integrated circuits referred to in the art as computers, but broadly refers to computers, processors, microcontrollers, microcomputers, programmable logic controllers, application specific integrated circuits, and other programmable circuits.

Set forth below is a description of an exemplary multislice CT system in accordance with one embodiment of the present invention. Although one embodiment of the system is described in detail below, it should be understood that many alternative embodiments of the inventions are possible. For example, although one particular detector and one particular pre-patient collimator are described, other detectors or collimators could be used in connection with the system, and the present invention is not limited to practice with any one particular type of detector. Specifically, the detector described below includes a plurality of modules and each module includes a plurality of detector cells. Rather than the specific detector described below, a detector which has non-segmented cells along the z-axis, and/or a detector which has multiple modules 20 with multiple elements along the x-axis and/or z-axis joined together in either direction to acquire multislice scan data simultaneously, can be utilized. Generally, the system is operable in a multislice mode to collect one or more slices of data. Axial and helical scans can be performed with the system, and cross section images of a scanned object can be processed, reconstructed, displayed and/or archived.

In some configurations of the present invention, the pitch of a scan is a variable in the sense that the location of the x-ray tube and detector relative to an image reconstruction plane is determined using a measured or estimated table position. In these configurations, the translatable table can move at a constant speed for part or all of a scan, but it is not constrained to do so as in a constant pitch scan. Unless otherwise specifically noted, scans in which the pitch of a scan is a variable in the above sense are intended to be included within the scope of the term "dynamical helical scan."

Furthermore, although system 10 is illustrated using an "open loop" control for the dynamic pitch scan. In many cases, the adjustment of the translatable table position and/or speed during the scan using a feedback loop is required. For example, based on the measured projections and other information, the helical pitch can be adjusted to obtain optimal clinical results, such as maximum contrast enhancement. In an embodiment using a closed loop feedback a comparator is used to compare the current table location to the desired table location to generate a position error which is transmitted to table motor controller 44.

Additionally, configurations of the present invention described herein have a constant gantry rotation speed during data collection, although a constant gantry rotation speed is not required to practice the present invention.

Figure 3:
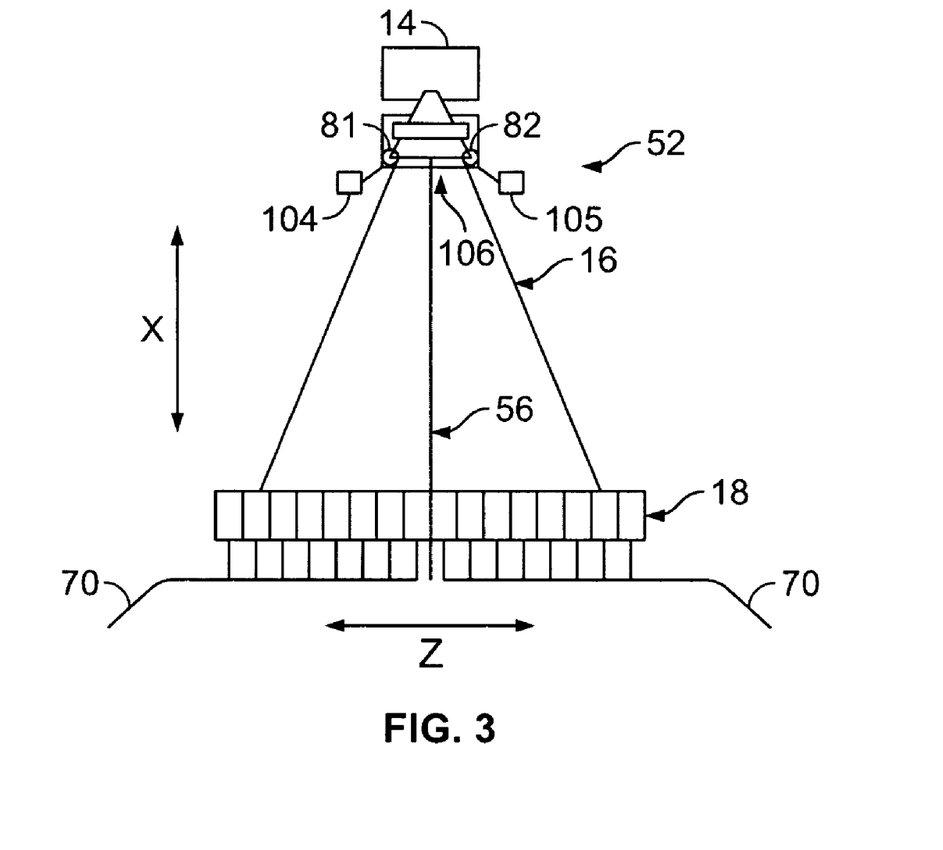
FIG. 3 is a schematic side view of a portion of an exemplary embodiment of CT imaging system 10.

FIG. 3 is a schematic side view of a portion of an exemplary embodiment of CT imaging system 10. Collimator 52 includes a first eccentric cam, shutter cam 81, and a second eccentric cam, tracking cam 82 for adjusting an aperture 106 between them. The position of cams 81 and 82 is controlled by a collimator controller (not shown in FIG. 3). Specifically, the collimator controller includes a cam drive or at least one cam motor 104 and/or 105, for altering the position of cams 81 and 82, respectively. In addition, in one embodiment, the collimator controller includes a processing unit, or logic circuitry for controlling the cam drive and exchanging information with x-ray controller 28. In an alternative embodiment, the collimator controller receives signals from sensors configured to determine a position of translatable table 46 and/or gantry 12. In another alternative embodiment, the cam drive may be controlled directly by radiation controller 28.

Cams 81 and 82 are positioned on opposing sides of fan beam axis 56 and may be independently adjusted with respect to the spacing between cams 81 and 82 and their location relative to fan beam axis 56. Cams 81 and 82 may be positioned with a single cam drive, or alternatively, each cam may be positioned with a separate cam drive. For example and in one embodiment, separate cam motors 104 and 105 are connected to respective cams 81 and 82 for precisely controlling the position of cams 81 and 82 so that each cam may be independently positioned. In other embodiments, collimator 52 may include additional cams and each cam may be coupled to a separate cam drive, for example cam motor or actuator, for altering the position of the cam. Cams 81 and 82 are fabricated from an x-ray absorbing material, for example, tungsten. Although collimator 52 is described as having a pair of eccentric cams 81 and 82, other configurations of collimator 52 are contemplated. Specifically, cams 81 and 82 may be configured as blades that may translate to change the collimation of beam 16 or may rotate to change the collimation of beam 16.

Figure 4:
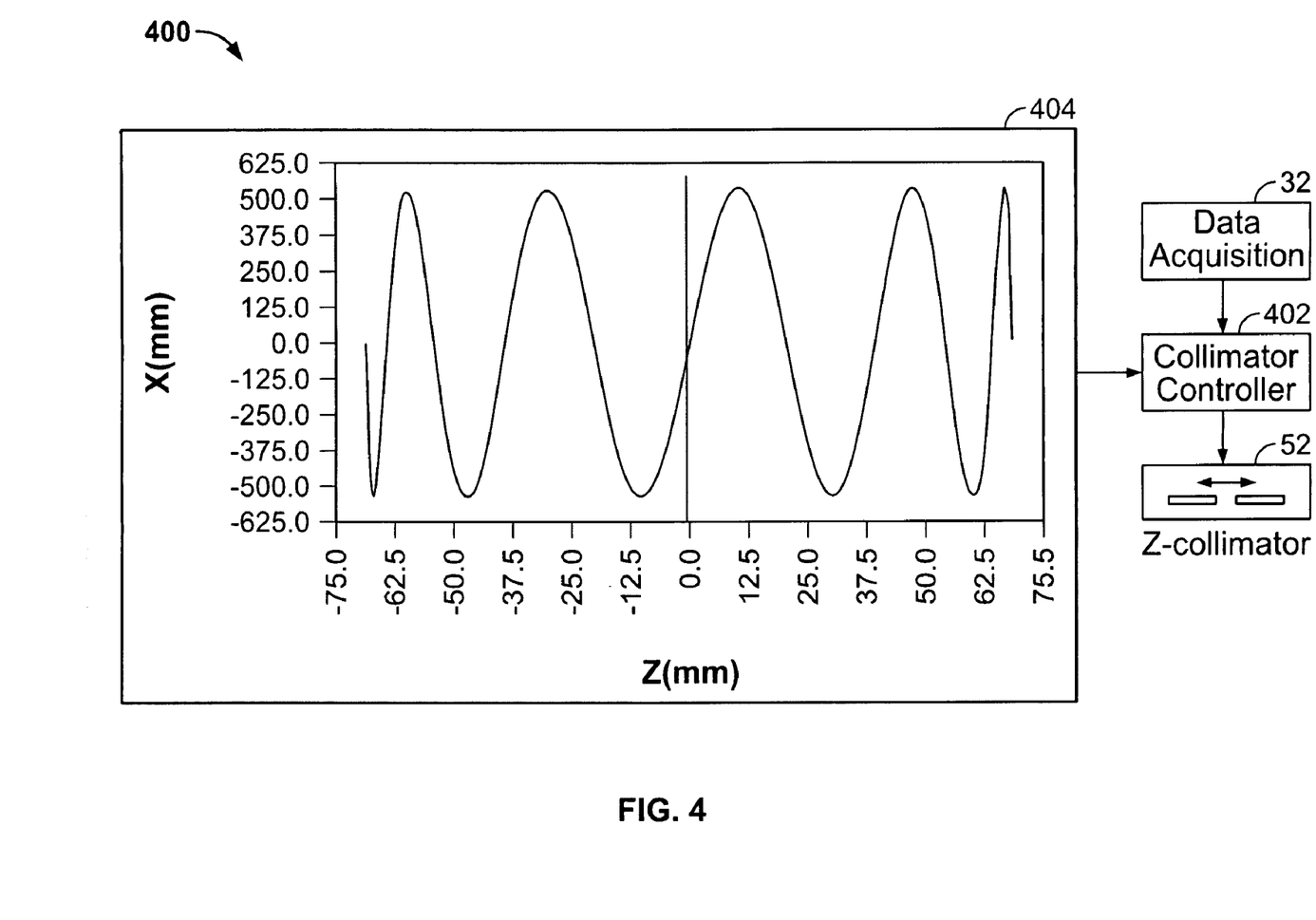
FIG. 4 is a schematic block diagram of an exemplary embodiment of a collimation system that may be used with the imaging system shown in FIG. 2.

FIG. 4 is a schematic block diagram of an exemplary embodiment of a collimation system 400 that may be used with system 10 (shown in FIG. 2). In the exemplary embodiment, collimator 52 is communicatively coupled to a collimator controller 402. Collimator controller 402 is configured to receive information 404 about a predetermined scan trajectory. In the exemplary embodiment, information 404 is in the form of a graph of coordinates of the trajectory. In an alternative embodiment, information 404 is in the form of coefficients of an equation describing the translational position of table 46 as a function of time or a rotation angle of gantry 12. For example, for a dynamic trajectory described by the equation:

$$z(s) = Tk\left(1 - \cos\left(\frac{s}{T}\right)\right) + v_0 s + \frac{1}{2}a_0 s^2 + z_0$$

The coefficients of this equation (T, k, $v_0$, $a_0$, $z_0$) are transmitted to collimator controller 402. In an alternative embodiment, information 404 is in the form of the actual table position in the Z-axis that is transmitted to collimator controller 402 to determine the position of collimator 52 required to achieve the desired collimation on detector 18.

Data acquisition system 32 is communicatively coupled to collimator controller 402, and transmits signals to collimator controller 402 indicative of the state of system 10, for example, DAS 32 receives a position of table 46 and/or gantry 12 and transmits the position data to collimator controller 402. Such information is in the form of a view number, time, and/or angular position of the gantry. Using such information and the trajectory, collimator controller 402 adjusts Z-aperture 106 of collimator 52 to illuminate only that portion of detector 18 that is used by the reconstruction algorithm.

As illustrated in FIGS. 1 and 2 in the attachments, the exact detector coverage required by the reconstruction algorithm varies at different points in the trajectory (a feature unique to the dynamic pitch case). In particular at the time instant indicated in FIG. 1, roughly 20 rows of the detector are required. In FIG. 2, on the other hand, only 8 rows are required. Based on the data samples required by the reconstruction algorithm (which can be computed from the formulae in Katsevich 2003), or some other algorithm (based on say, the Z-extent of the projected helical trajectory with some multiplicative factor), the collimator controller determines for a given view what collimation is required on the detector.

Figure 5:
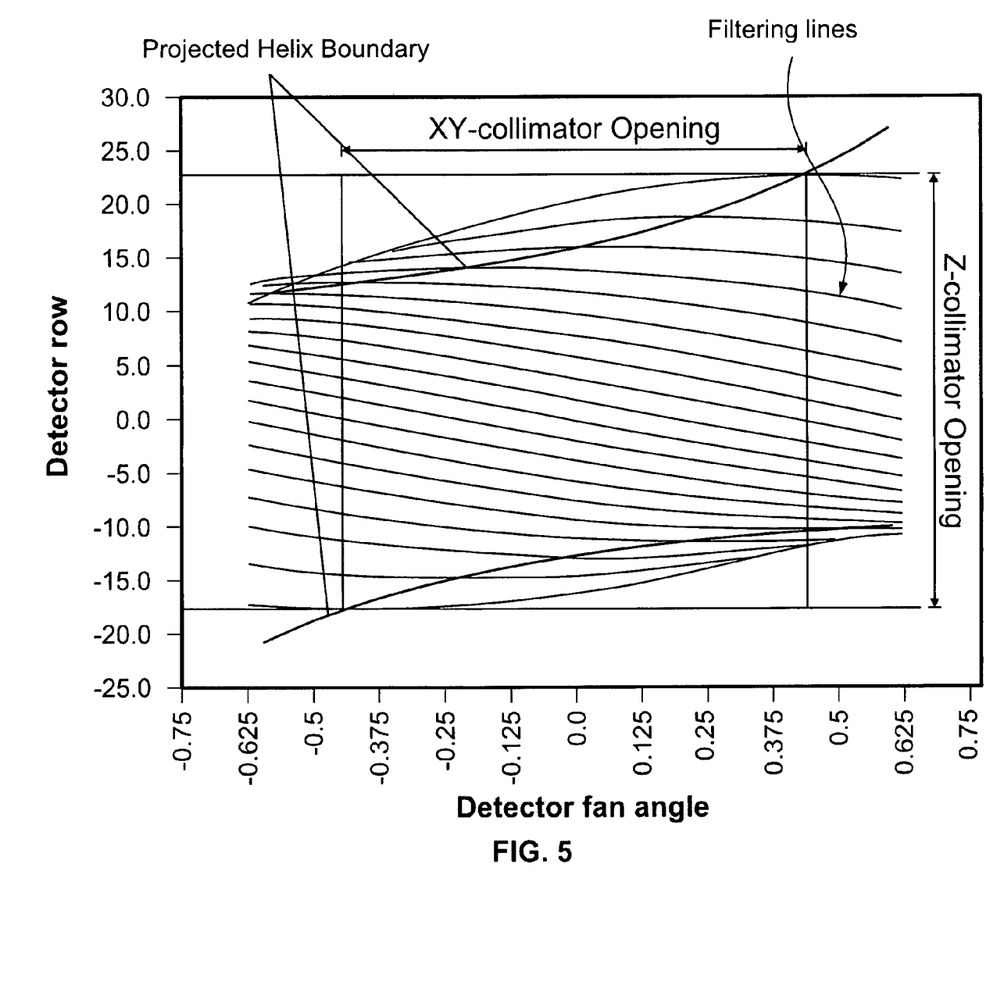
FIG. 5 illustrates a Z-collimator opening during a first portion of a dynamic pitch scan.

FIG. 5 illustrates a Z-collimator opening during a first portion of a dynamic pitch scan. A feature that is unique to dynamic path scanning is that the exact detector coverage required by the reconstruction algorithm varies at different points in the trajectory. Specifically, at the time instant illustrated in FIG. 5, roughly 20 rows of the detector are used. Based on the data samples required by the reconstruction algorithm or an algorithm based on, for example, the Z-extent of the projected helical trajectory with some multiplicative factor, collimator controller 402 determines, for a particular view, the collimation requirements on the detector.

Figure 6:
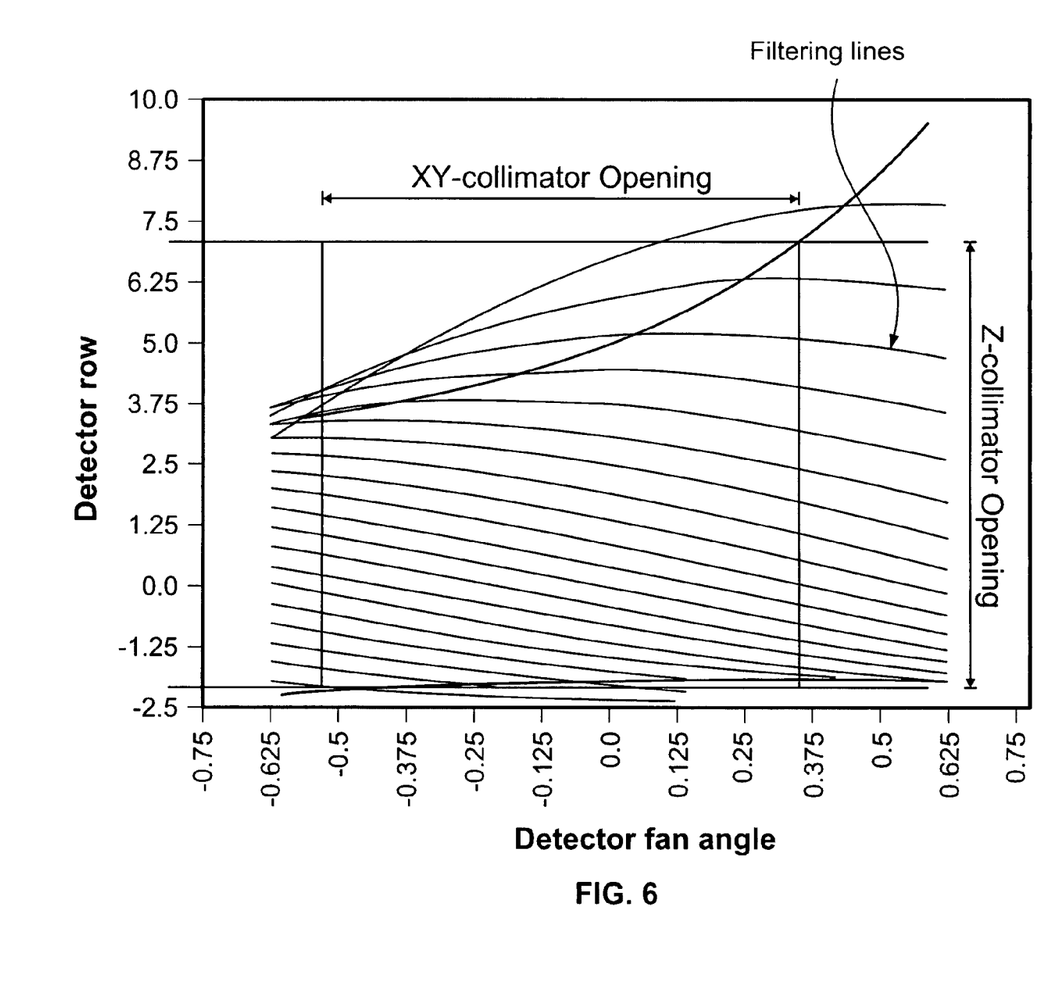
FIG. 6 illustrates a Z-collimator opening during a second portion of the dynamic pitch scan.

FIG. 6 illustrates a Z-collimator opening during a second portion of the dynamic pitch scan. At the time instant of the trajectory illustrated in FIG. 6 only 8 rows of the detector are used because of the exact detector coverage needed by the reconstruction algorithm varies at different points in the trajectory.

Although the above-described configurations utilizing a scanning CT imaging system, it will be appreciated that the invention is not limited to such systems. For example, other imaging modalities, such as MR, can be used to acquire images with a dynamically changing table speed.

It will be appreciated that a technical effect of the configurations of the present invention described herein is the scanning and reconstruction of an object or patient utilizing a dynamical helical scan and a translatable table.

The above-described embodiments of an imaging system provide a cost-effective and reliable means for imaging a patient. More specifically, the imaging system includes dynamically positionable collimator that shapes the x-ray beam in the z-axis such that a dose savings and a smaller dataset are achieved.

Exemplary embodiments of imaging system methods and apparatus are described above in detail. The imaging system components illustrated are not limited to the specific embodiments described herein, but rather, components of each imaging system may be utilized independently and separately from other components described herein. For example, the imaging system components described above may also be used in combination with different imaging systems. A technical effect of the various embodiments of the systems and methods described herein include facilitating reducing x-ray dosage to patients during a scan.

While the invention has been described in terms of various specific embodiments, those skilled in the art will recognize that the invention can be practiced with modification within the spirit and scope of the claims.

What is claimed is:

1. A collimation system for controlling x-ray exposure during a dynamic pitch helical scan using a translatable table comprising:
   a collimator positioned between an x-ray source and an object to be scanned configured to shutter an x-ray fan beam generated by the x-ray source to at least one of translate the x-ray fan beam along a z-axis of the scan and vary the width of the x-ray beam along the z-axis; and
   a collimator controller configured to dynamically position the collimator using at least one of predetermined trajectory of the translatable table and an actual position of the translatable table.

2. A collimation system in accordance with claim 1 further comprising a table position encoder configured to determine an actual position of the translatable table.

3. A collimation system in accordance with claim 2 wherein said collimator controller is configured to determine at least one of a velocity of the translatable table and an acceleration of the translatable table.

4. A collimation system in accordance with claim 1 further comprising a trajectory selector configured to store at least one of a predetermined trajectory and a received trajectory.

5. A collimation system in accordance with claim 1 wherein the trajectory is described by the coefficients of an equation describing the translational position of the translatable table as a function of at least one time and a gantry rotation angle.

6. A collimation system in accordance with claim 5 wherein the coefficients are transmitted to the collimator controller at least one of before the beginning of the scan and during the scan.

7. A collimation system in accordance with claim 5 wherein the translational position of the translatable table is described by:

$$z(s) = Tk\left(1 - \cos\left(\frac{s}{T}\right)\right) + v_0 s + \frac{1}{2}a_0 s^2 + z_0,$$

wherein T represents a trajectory selected, k represents a constant, $v_0$ represents an initial velocity, $a_0$ represents an initial acceleration, and $z_0$ represents an initial position.

8. A system for reducing x-ray exposure in a computed tomography system, the computed tomography system including an x-ray source, a detector array comprising a plurality of detector cells extending in a z-axis, and a pre-patient collimator, said system configured to:
   determine a position of a patient table along the z-axis; and
   position said collimator to define a thickness of a fan beam to be directed towards an object to be imaged using at least one of the position of the patient table and a predetermined table trajectory.

9. A system in accordance with claim 8 wherein said system is configured to determine a position of a patient table using a position encoder.

10. A method of controlling x-ray dosage in a computed tomography (CT) system including a patient table translatable along a z-axis at a dynamically changeable rate and a collimator that defines an aperture, said method comprising:
    receiving data concerning a scan trajectory of the patient table;
    determining an amount of collimation on the detector using a selected image reconstruction algorithm requirement; and
    positioning the collimator aperture such that the determined collimation is maintained during the scan.

11. A method in accordance with claim 10 wherein receiving data concerning a scan trajectory of the patient table comprises receiving a selectable one of a plurality of predetermined scan trajectories.

12. A method in accordance with claim 10 wherein receiving data concerning a scan trajectory of the patient table comprises determining an adaptive scan trajectory determined using scan data received during the scan.

13. A method in accordance with claim 10 wherein receiving data concerning a scan trajectory of the patient table comprises determining an equation that describes the translational position of the patient table as a function of at least one of time and an angle of rotation of a gantry portion of the CT system.

14. A method in accordance with claim 13 wherein receiving data concerning a scan trajectory of the patient table comprises receiving coefficients of the terms of the equation.

15. A method in accordance with claim 10 further comprising describing a translational position of the patient table using:

$$z(s) = Tk\left(1 - \cos\left(\frac{s}{T}\right)\right) + v_0 s + \frac{1}{2}a_0 s^2 + z_0,$$

wherein T represents a trajectory selected,
k represents a constant,
$v_0$ represents an initial velocity,
$a_0$ represents an initial acceleration, and
$z_0$ represents an initial position.

16. A method in accordance with claim 15 further comprising receiving coefficients T, k, v0, a0, and z0 by a collimator controller.

17. A method in accordance with claim 10 further comprising receiving coefficients of the terms of the equation by a collimator controller.

18. A method in accordance with claim 10 wherein determining an amount of collimation of the detector comprises receiving at least one of a current position of the patient table and a current angular position of the gantry.

19. A method for reducing x-ray exposure in a computed tomography (CT) system, the CT system including a gantry having at least an x-ray source, a detector array comprising a plurality of detector cells extending in a z-axis, a patient table translatable in the Z axis, and a collimator positioned between the x-ray source and the patient table, said method comprising:
    receiving coefficients of the terms of an equation that describes the translational position of the patient table as a function of at least one of time and an angle of rotation of a gantry portion of the CT system, by a collimator controller;
    determining an amount of collimation of the detector for an image reconstruction algorithm selected; and
    adjusting the aperture of the collimator in the Z direction to illuminate a portion of the detector that is used by the reconstruction algorithm.

20. A method in accordance with claim 19 wherein determining an amount of collimation of the detector comprises receiving at least one of a current position of the patient table and a current angular position of the gantry.

* * * * *

UNITED STATES PATENT AND TRADEMARK OFFICE
CERTIFICATE OF CORRECTION

PATENT NO. : 7,242,749 B2
APPLICATION NO. : 11/273851
DATED : July 10, 2007
INVENTOR(S) : Hsieh et al.

It is certified that error appears in the above-identified patent and that said Letters Patent is hereby corrected as shown below:

On Title Page, item 73 after "Assignee: General Electric Company, Schenectady, NY (US)", insert --; University of Central Florida Research Foundation, Inc., Orlando, FL (US)--

Signed and Sealed this

Fifth Day of August, 2008

JON W. DUDAS
*Director of the United States Patent and Trademark Office*